United States Patent [19]

Badger et al.

[11] Patent Number: 5,030,204
[45] Date of Patent: Jul. 9, 1991

[54] GUIDING CATHETER WITH CONTROLLABLE DISTAL TIP

[75] Inventors: Rodney S. Badger, Morago; Lawrence D. Wasicek, Sunnyvale, both of Calif.

[73] Assignee: Advanced Cardiovascular Systems, Inc., Santa Clara, Calif.

[21] Appl. No.: 475,703

[22] Filed: Feb. 6, 1990

Related U.S. Application Data

[63] Continuation of Ser. No. 250,709, Sep. 28, 1988, Pat. No. 4,890,577.

[51] Int. Cl.$^5$ ............................................. A61M 37/00
[52] U.S. Cl. .................................... 604/95; 604/280; 128/657
[58] Field of Search ............................... 604/95, 280; 128/656-658, 772

[56] References Cited

U.S. PATENT DOCUMENTS

| | | | |
|---|---|---|---|
| 2,688,329 | 9/1959 | Wallace | 604/95 |
| 4,586,923 | 5/1986 | Gould et al. | 604/95 |
| 4,641,654 | 2/1987 | Sampson et al. | 604/95 |
| 4,740,195 | 4/1988 | Larciaro | 604/95 |

Primary Examiner—Stephen C. Pellegrino
Assistant Examiner—Michael Rafa
Attorney, Agent, or Firm—Fulwider, Patton, Lee & Utecht

[57] ABSTRACT

Guiding catheter and method of using the same in a cardiovascular procedure such as coronary angioplasty. The catheter has an elongated shaft with a deflectable distal portion. One lumen extends through the elongated shaft to form a passageway through which a dilatation catheter can be introduced. A second smaller lumen extends through the shaft to form a passageway for a control line which passes therethrough and which is connected to the distal tip. Proximal movement of the control line decreases the included angle between the distal portion and the main portion of the shaft. Pull on the control line also exerts a force on the distal portion of the guiding catheter which transmits a resultant axial force to push the catheter disposed within the first lumen. Pull on the control line also allows for catheter tip configuration adjustment thereby enabling the catheter to engage a difficult coronary ostium. In the disclosed embodiments, the distal portion is formed in two sections. Pulling the control line decreases the included angles between the distal sections and the main sections while the distal portion is positioned within a patient. The axial force is particularly advantageous with dilatation catheters to aid in directing the distal end thereof across a lesion.

5 Claims, 2 Drawing Sheets

GUIDING CATHETER WITH CONTROLLABLE DISTAL TIP

This is a continuation of application Ser. No. 07/250,709, filed Sept. 28, 1988 now U.S. Pat. No. 4,898,577.

BACKGROUND OF THE INVENTION

This invention generally relates to vascular catheters and particularly to guiding catheters for the placement of intracoronary devices within a patient's vascular system such as dilatation catheters in procedures such as percutaneous transluminal coronary angioplasty (PTCA).

In the classic PTCA procedure, a guiding catheter having preformed distal tip is percutaneously introduced into the cardiovascular system of a patient and advanced therein until the distal tip thereof is in the ostium of the desired artery. A guidewire and a dilatation catheter having a balloon on the distal end thereof are introduced through the guiding catheter with the guidewire slidably disposed within an inner lumen of the dilatation catheter. The guidewire is first advanced into the patient's coronary vasculature until the distal end of the guidewire crosses the lesion to be dilated, then the dilatation catheter is advanced over the previously introduced guidewire until the dilatation balloon is properly positioned across the lesion. Once in position across the lesion, the balloon is inflated predetermined size with radiopaque liquid at relatively high pressures (e.g., generally 4–12 atmospheres) to compress and split the atherosclerotic plaque of the lesion against the inside of the artery wall to thereby dilate the lumen of the diseased artery. The balloon is then deflated so that the dilatation catheter can be removed and blood flow resumed through the dilated artery.

Further details of guiding catheters, dilatation catheters, guidewires, and the like for angioplasty procedures can be found in Simpson-Robert U.S. Pat. No. 4,323,071; Lundquist U.S. Pat. No. 4,439,185; Enzmann et al. U.S. Pat. No. 4,468,224; Samson et al. U.S. Pat. No. 4,516,972; Samson et al. U.S. Pat. No. 4,538,622; Samson U.S. Pat. No. 4,582,185; Simpson U.S. Pat. No. 4,616,652; and Powell U.S. Pat. No. 4,638,805 which are hereby incorporated herein in their entirety by reference thereto.

Frequently, sufficient force cannot be applied to the proximal end of a dilatation catheter to advance the balloon thereof across a lesion. Additional axial force can be supplied to the dilatation catheter by buttressing the guiding catheter against a wall of the aorta, by deep seating the guiding catheter tip well into the coronary ostium, by choosing guiding catheter with a different distal configuration, increasing the stiffness of the guiding catheter. However, in practice, these methods are not always successful and no dilatation of stenosis can occur unless the balloon crosses the lesion.

Steerable dilatation cathethers with built-in or fixed guidewires or guiding elements are used with greater frequency because their deflated profiles are generally smaller than conventional dilatation catheters with movable guidewires having the same inflated balloon size. Moreover, the fixes guiding elements in the steerable dilatation catheters provide greater pushability which allows them to cross such tighter lesions than dilatation catheters with movable guidewires. Further details of steerable dilatation catheters may be found in Samson U.S. Pat. No. 4,582,181, Frisbie et al. U.S. Pat. No. 4,619,263, Samson et al. U.S. Pat. No. 4,641,654, and Frisbie et al. U.S. Pat. No. 4,664,113 which are hereby incorporated in their entirety by reference thereto.

While the tubular members forming the catheter body utilizing a movable guidewire could be made from stiffer material or thicker walled tubing to increase the pushability of the catheter, such added stiffness would reduce the flexibility of the distal end of the catheter which allows the catheter to pass through the tortuous passageways of a patient's vascular system.

Other types of intracoronary catheters such as those used for mechanical and laser based atherectomy procedures and angioscopic catheters generally have much stiffer shafts than balloon dilatation catheters. As a result, the guiding catheter frequently is not sufficiently strong to maintain its preformed distal shape when these stiffer catheters are disposed within the guiding catheter and advanced into and through coronary stenoses. This makes the placement of such stiffer catheters much more difficult.

In some situations, the preformed distal curvature of the guiding catheters may not be the exact curvature needed for the placement of the distal tip in the desired location within the patient's cardiovascular system.

When many of the aforesaid problems occur, the only solution is to withdraw the guiding catheter from the patient's body and replace it with a guiding catheter having a different curvature or stiffness. This recatheterization not only increases the time required for the procedure but it also adds further arterial trauma. Withdrawal of a guiding catheter necessitates withdrawing the guidewire and balloon dilatation catheter out of the coronary stenosis, which increases the risk of acute coronary closure and myocardial infarction if the coronary stenosis has not yet been properly dilated.

What has been needed and heretofore unavailable is guiding catheter which has a distal portion or segment, the shape and stiffness of which can be changed from the proximal end after it has been inserted into the patient and which can aid in providing support to a dilatation catheter when the balloon thereof is being advanced across a tight lesion. The present invention satisfies this need.

SUMMARY OF THE INVENTION

The present invention is directed to an improved guiding catheter with a deflectable distal segment which is operable from the proximal end thereof and which has sufficient stiffness or strength to support dilatation catheters and other type catheters for their proper placement within a patient's coronary vasculature.

The guiding catheter in accordance with the invention generally comprises an elongated tubular member having proximal and distal portions, with the distal portion preformed into at least one section which is at an angle from the main tubular section or an adjacent preformed section, or both. The elongated tubular member has at least two lumens extending along the length thereof, a first relatively large diameter lumen, which is adapted to receive various types of catheters, guidewires, and the like, and a second relatively small diameter lumen, which has disposed therein a control line such as wire or cable which extends and is secured to the distal tip of the tubular member. Pulling tension on the control line causes one or more of the preformed articulated distal sections to be brought closer together, reducing the included angle therebetween and thereby causing deflection of the catheter tip.

The articulated, relatively stiff distal sections allow the shape of the distal portion of the guiding catheter to be changed from the proximal end to a more desirable configuration or to be returned to the preformed shape should the tip be deformed once the catheter is disposed within a patient. Moreover, this deflectability, which strengthens and stiffens the guiding catheter, can also be used to add an axial force to a dilatation catheter disposed therein when pushing the dilatation catheter across a tight lesion.

These and other advantages of the invention will become more apparent from the following detailed description of the invention including the accompanying exemplary drawings.

DETAILED DESCRIPTION OF THE INVENTION

Figure 1:
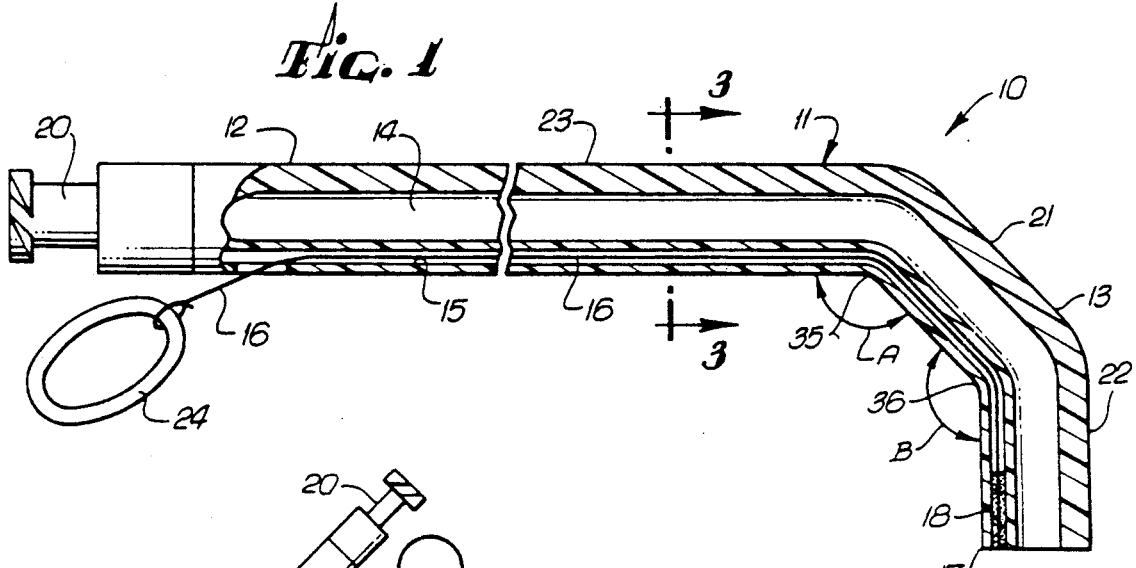
FIG. 1 is a centerline sectional view of an articulated guiding catheter embodying features of the invention.

FIG. 1 illustrates a guiding catheter 10 embodying features of the invention which generally comprises an elongated tubular member 11 with a proximal portion 12 and a distal portion 13. A first relatively large diameter longitudinally extending lumen 14 and a second relatively small diameter longitudinally extending lumen 15 are provided in tubular member 11. The diameter of lumen 14 is of relatively large diameter to facilitate the passage of guidewires, dilatation catheters and the like therethrough. Lumen 15 is of smaller diameter than lumen 14 nd has disposed therein a control line 16 which is fixed to the distal tip 17 by adhesive 18. A Luer fitting 20 is provided at the proximal end of the tubular member 11 and is in communication with lumen 14 for connecting the catheter to an adapter (not shown).

The distal portion 13 of the tubular member 11 has two articulated sections 21 and 22 which are relatively stiff and preformed into a desired shape with included angles A and B therebetween. If desired, the material at the functions between sections 21 and 22 and section 21 and the main section 23 can be made more flexible to facilitate the bending of sections 21 and 22. For example, the entire catheter can be formed from suitable plastic materials a unitary structure with the junctions between the sections being irradiated or otherwise treated to make them more flexible when the distal sections are preformed into the desired shape. Alternatively, the main section 23 and the distal tip sections 21 and 22 and the joints therebetween can be formed separately and joined together by suitable means such as heat sealing or adhesive bonding. While the guiding catheter 10 is shown in the drawings in a classic Judkins left configuration, it should be apparent that other preformed configurations can be made with various numbers of articulated sections.

A control line 16 extends through lumen 15. It is secured at the distal end thereof to the distal tip 17 by adhesive 18 and ring 24 is connected to the proximal end of the control line 16 to facilitate applying tension thereto when deflecting the distal sections 21 and 22. The control line 16 may be fabricated of any suitable material such as a metal or plastic and may be in the form of a flexible wire or cable.

The guiding catheter 10 can be fabricated of a variety of suitable materials, and it can be formed by any suitable process such as extrusion. In the embodiment shown in FIG. 3, the tubular member 11 comprises a tubular sheath 25 of generally circular cross section which is formed of braided or wound aramid fibers, such as DuPont's Kevlar fibers, impregnated with a plastic material, such as polyurethane or epoxy resin. The large lumen 14 is formed with a liner 26 of lubricious material such as polytetrafluoroethylene (Teflon) which is positioned eccentrically within the tubular sheath 25. The smaller lumen 15 is formed by a polyimide tube 27 which is positioned in the crescent-shaped space 28 between Teflon liner 26 and sheath 25. A suitable polyimide tubing is the Micro-Bore TM tubing sold by Polymicro Technologies Phoenix, Ariz. A polyethylene jacket 29 surrounds the tubular sheath 25.

Figure 4:
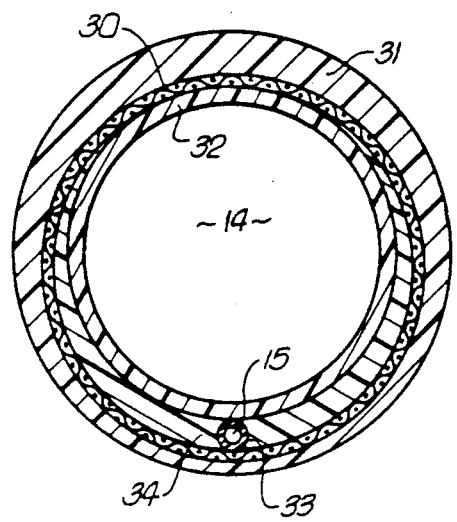
FIG. 4 is a cross-sectional view similar to that shown in FIG. 3 of an alternative construction.

An alternate embodiment is shown in FIG. 4 wherein the shaft 11 of catheter 10 has a tubular sheath 30 of wound or braided aramid fibers, such as Kevlar, impregnated with polyurethane or with epoxy resin. A layer or jacket 31 of polyethylene is provided on the outside and an inner layer 32 of Teflon is positioned concentrically within the sheath 30. A small diameter tube 33, preferably formed of polyimide which defines small lumen 15 is disposed in space 34 between sheath 30 and Teflon lining 32. The space 33 can be filled with any suitable filler material.

Figure 3:
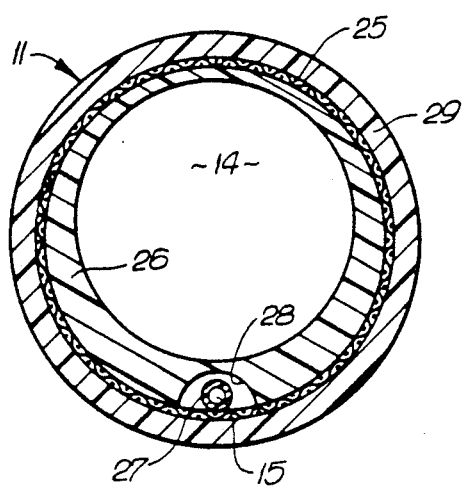
FIG. 3 is a cross-sectional view taken along line 3—3 in FIG. 1.

In the embodiments shown in FIGS. 3 and 4, the tubular shafts 11 and 20 typically have outer diameters on the order of 0.118 inch. The lumen 14 has a diameter on the order of 0.078 inch and lumen 15 has a diameter on the order of 0.010 inch. Sheaths 25 and 30 have wall thicknesses on the order of 0.006 inch. The Teflon layers 26 and 32 have a minimum thickness on the order of 0.003 inch. Control line 16 has a diameter on the order of 0.004 inch and polyimide tubes 27 and 33 have a wall thickness on the order of 0.001 inch.

Figure 2:
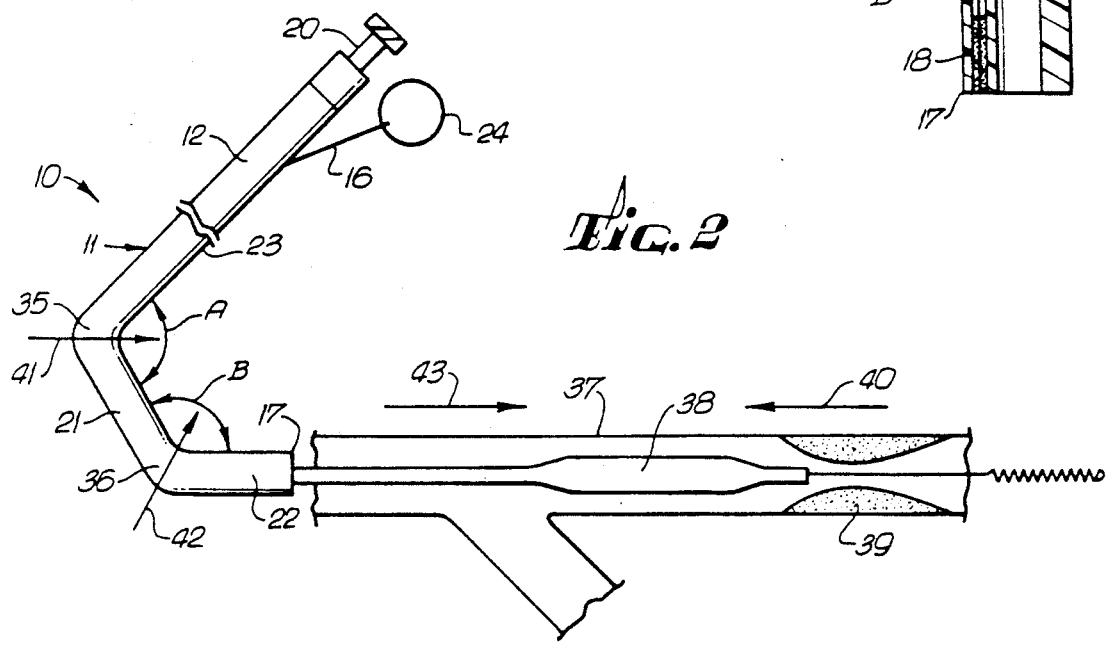
FIG. 2 is a schematic operational view, illustrating the operation of the articulated guiding catheter of FIG. 1.

The deflection of the distal portions 21 and 22 of catheter 10 is best illustrated in FIG. 2. By pulling tension via a device on the proximal end of control line 16 at the proximal end of the catheter 10, the catheter flexes at location 35 between the main section 23 and distal section 21 and location 36 between distal sections 21 and 22 there by decreasing the included angles A and B.

The deflection of the articulated sections 21 and 22 can be used to guide the distal tip 13 of the guiding catheter to its proper position within a coronary artery 37 and the stiffness imparted to the distal portion of the guiding catheter can be used to assist a dilatation catheter 38 to be advanced through the guiding catheter 10 and across a lesion 38. In this latter instance, when further movement of dilatation catheter 38 is resisted by a force represented by the arrow 40, pulling on the proximal end of the control line 16 produces forces represented by arrows 41 and 42 at locations 34 and 35 which combine to produce a resultant force having an axial component represented by arrow 43. The added axial force 43 can be sufficient to advance the dilatation catheter 38 across the lesion 39.

Usually, the guiding catheter 10 and dilatation catheter 38 are introduced together into the cardiovascular system of a patient with the distal end portion of the dilatation catheter 38 retracted from distal tip 17 of the guiding catheter 10. As the catheters are percutaneously introduced into the patient, the configuration of the distal tip of catheter 10 can be changed by pulling proximally on control line 16 outside of the patient's body to change the angles A and B between the main section 23 and the distal sections 21 and 22 to guide the distal tip 17 to the desired location.

When a stiff catheter or other intracoronary device deforms the preformed distal portion 13 with its passage, the control line can be proximally to return the shape of the distal portion 13 to its performed shape.

Figure 5:
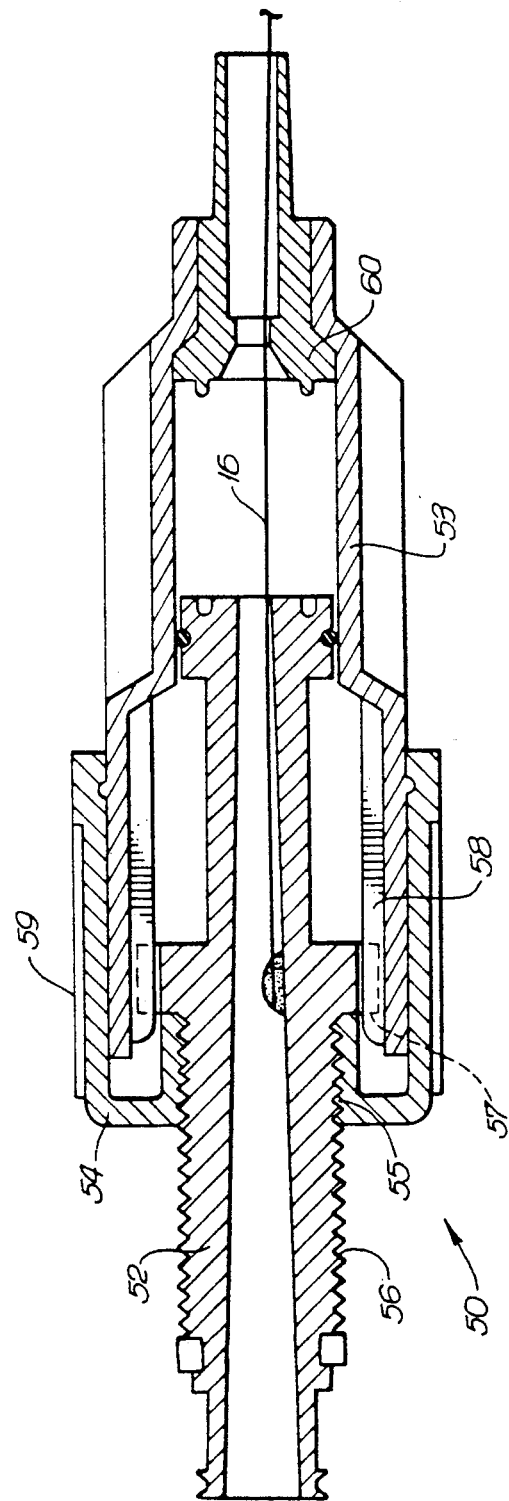
FIG. 5 is a cross-sectional view of a manipulator for applying tension to the control line in the guiding catheter.

FIG. 5 illustrates a presently preferred manipulator 50 which is adapted to move control wire 16 and thereby change the shape of the distal end of the guiding catheter (not shown) in accordance with the invention. The proximal end 51 of control wire 16 is secured to the interior of movable threaded member 52 which is slidably disposed within manipulator housing 53. A collar 54 is rotatably mounted about the proximal end of manipulator housing 53 and is provided with threads 55 on the interior thereof which are adapted to engage the exterior threaded section 56 on the movable member 52. The movable member 52 is provided with a plurality of extensions 57 adjacent the threaded section 56 thereof which are adapted to slidably engage ribs or guides 58 provided on the interior surface of the housing 53.

Manual rotation of collar 54 causes relative movement between the movable member 52 and the housing 53. The outer surface 59 of collar 54 can be knurled as shown to facilitate the manual rotation thereof. The outer surface of the movable member 52 on the end thereof opposite the threaded section is provided with a ring to prevent loss of fluids. A stepping element 60 is provided in the distal end of the manipulator housing 53 to prevent further distal movement of the movable member 52. Extensions 57 stop the proximal movement thereof. To operate the manipulator 50, the collar 54 is rotated clockwise to apply tension to control wire 16 and counterclockwise to release applied tension. The various components of manipulator 50 can be made of suitable plastic materials such as polyethylene.

It is apparent from the foregoing that a new and improved guiding catheter and method of using the same have been provided. While only certain presently preferred embodiments have been described in detail, as will be apparent to those familiar with the art, certain changes and modifications can be made without departing from the scope of the invention as defined by the following claims.

What is claimed is:

1. A manipulator for pushing and pulling an elongated member within an inner lumen of an intravascular catheter having proximal and distal ends comprising:
   (a) an elongated housing having opposing ends and an interior chamber;
   (b) a collar which has a central passageway with female threads therein and which is rotatably mounted on one of the ends of the elongated housing;
   (c) a longitudinally movable member which has male threads, which is disposed within the interior chamber of the elongated housing and which is adapted to extend through the central passageway of the collar, and threadably engage the threads therein;
   (d) an elongated member movably disposed within the inner lumen extending through the intravascular catheter; and
   (e) means to change the relative axial position of the elongated member within the inner lumen of the intravascular catheter, thereby causing movement of the elongated member therein.

2. The manipulator of claim 1 wherein the elongated member extends through an aperture in one end of the housing.

3. The manipulator of claim 2 wherein the interior of the housing is provided with longitudinally extending ribs on the inner surface of the housing which engage radial extensions on portions of the longitudinally movable member to guide the axial movement of the longitudinally movable member therein.

4. The manipulator of claim 2 wherein the longitudinally movable member has a central passageway in fluid communication with the interior of the housing.

5. The manipulator of claim 4 wherein the catheter has a proximal end which is secured to the distal end of the housing and which is in fluid communication with the interior of the housing through the aperture in one of the ends of the housing.

* * * * *

UNITED STATES PATENT AND TRADEMARK OFFICE
CERTIFICATE OF CORRECTION

PATENT NO. : 5,030,204                                    Page 1 of 2
DATED      : July 9, 1991
INVENTOR(S): Rodney S. Badger, et al It is certified that error appears in the above-indentified patent and that said Letters Patent is hereby corrected as shown below:

Title page, item [75]

Inventors: add Bruce H. Wand of San Jose, California

COLUMN 1

Line 17: insert -- a -- after "having" and before "preformed".
  Line 30: insert -- to a -- after "inflated" and before "predetermined".
  Line 55: insert -- or by -- after "configuration," and before "increasing".
  Line 66: "such" should read -- much --.

COLUMN 3

Line 46: "nd" should read -- and --.
  Line 55: "functions" should read --junctions --.

UNITED STATES PATENT AND TRADEMARK OFFICE
CERTIFICATE OF CORRECTION

PATENT NO.   : 5,030,204
DATED        : July 9, 1991
INVENTOR(S)  : Rodney S. Badger, et al It is certified that error appears in the above-indentified patent and that said Letters Patent is hereby corrected as shown below:

COLUMN 5
Line 17: insert -- pulled -- after "be" and before "proximally".

Signed and Sealed this

Twenty-fourth Day of August, 1993

Attest:

BRUCE LEHMAN

*Attesting Officer*          *Commissioner of Patents and Trademarks*